United States Patent [19]

Kleeman et al.

[11] Patent Number: 5,169,841
[45] Date of Patent: Dec. 8, 1992

[54] RENIN INHIBITORS

[75] Inventors: Heinz-Werner Kleeman, Kelsterbach; Hansjörg Urbach; Dieter Ruppert, both of Kronberg/Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 266,960

[22] Filed: Nov. 3, 1988

[30] Foreign Application Priority Data

Nov. 5, 1987 [DE] Fed. Rep. of Germany ....... 3737498
May 31, 1988 [DE] Fed. Rep. of Germany ....... 3818436

[51] Int. Cl.$^5$ .................. A61K 31/69; A61K 31/698; C07D 333/58
[52] U.S. Cl. ........................................ 514/63; 514/64; 514/2; 549/4; 549/213; 518/110; 518/405; 564/8; 558/288; 558/289; 546/13; 562/7
[58] Field of Search ................... 549/4, 213; 548/405, 548/110; 546/13; 562/7; 558/288, 280; 564/8; 514/64, 2, 63; 544/229

[56] References Cited

U.S. PATENT DOCUMENTS 4,499,082  2/1985  Shenvi et al. ........................... 514/2

FOREIGN PATENT DOCUMENTS 0145441  6/1985  European Pat. Off. ................ 514/2
0293881  12/1988  European Pat. Off. ................ 514/2
0354522  2/1990  European Pat. Off. ................ 514/2

OTHER PUBLICATIONS

Smith, et al., "Principles of Biochemistry: Mammalian Biochemistry," 7th ed., pp. 158-163, McGraw-Hill Book Co., New York (1983).
Hui et al., J. Med. Chem., vol. 30, pp. 1287-1295 (1987).
J. Med. Chem., 1985, vol. 28, pp. 1917-1925, American Chem. Soc., D. H. Kinder et al., "Acylamino Boronic Acids and Difluoroborane . . .".

Primary Examiner—Richard L. Raymond
Assistant Examiner—Mark W. Russell
Attorney, Agent, or Firm—Finnegan, Henderson, Farabow, Garrett and Dunner

[57] ABSTRACT

The invention relates to compounds of the formula 1

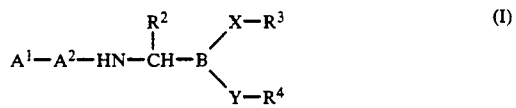

in which $A^1$ denotes a radical of the formulae

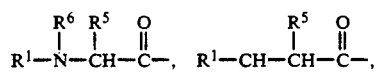

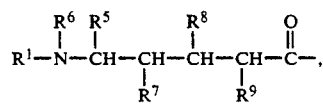

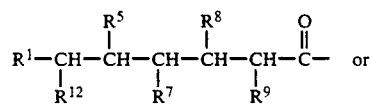

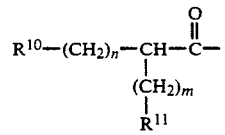

$A^2$ is absent or represents a radical of the formula

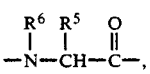

$R^2$, $R^3$ and $R^4$ are as defined in the specification, and X and Y, independently of one another, represent —O— or —NR$^{13}$—, and to the salts thereof. Also described is a process for the preparation of the compounds of the formula 1, corresponding pharmaceutical products, and the use thereof as medicines, and intermediates for the preparation of these compounds.

4 Claims, No Drawings

RENIN INHIBITORS

The invention relates to α-amino boronic acid derivatives which inhibit the action of the natural enzyme renin.

Elastase-inhibiting α-amino boronic acid peptides are described in U.S. Pat. No. 4,499,082.

The structure/activity relations in the area of renin inhibitors are discussed in J. Med. Chem. 30, 1287 (1987). Particular attention is paid tot he fact that potent inhibitors cannot dispense with binding to the P2' and P3' cavities of renin. This is why a deficiency associated with the renin inhibitors known to date is a high molecular weight and, resulting from this, inadequate enteral bioavailability and rapid excretion with the bile. The only exception takes the form of aldehydes with a renin inhibitory action, but these in turn are chemically unstable and tend to epimerize.

For the first time, stable, non-epimerizing, potent renin inhibitors which dispense with binding to the P' cavities of the enzyme, and thus meet the basic requirements for high enteral bioavailability, have been found.

The invention relates to compounds of the formula I

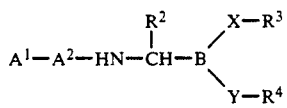

in which
$A^1$ denotes a radical of the formulae II, III, IV, V or VI

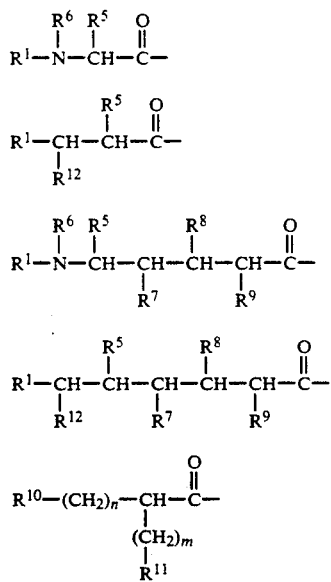

in which
$R^1$ $a_1$) denotes hydrogen, $(C_1-C_{12})$-alkyl which is optionally singly or doubly unsaturated and is optionally substituted by up to 3 identical or different radicals from the series comprising hydroxyl, $(C_1-C_7)$-alkoxy, carbamoyl, $(C_1$-14 $C_8)$-alkanoyloxy, carboxyl, $(C_1-C_7)$-alkoxycarbonyl, F, Cl, Br, I, amino, amidino which can optionally be substituted by one, two or three $(C_1-C_8)$-alkyl radicals, or guanidino which can optionally be substituted by one, two, three or four $(C_1-C_8)$-alkyl radicals, or $(C_1-C_7)$-alkylamino, di-$(C_1-C_7)$-alkylamino, $(C_1-C_5)$-alkoxycarbonylamino, $(C_7-C_{15})$-aralkoxycarbonylamino and 9-fluorenylmethoxycarbonylamino; or denotes mono-, bi- or tricyclic $(C_3-C_{18})$-cycloalkyl, $(C_3-C_{18})$-cycloalkyl$(C_1-C_6)$-alkyl or $(C_6-C_{14})$-aryl, the cycloalkyl moiety optionally being substituted by $(C_1-C_6)$-alkyl, and aryl optionally being substituted by one or two identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino, anilino which is optionally substituted with up to 2 halogen atoms, and trifluoromethyl; or denotes $(C_6-C_{14})$-aryl-$(C_1-C_6)$-alkyl in which the aryl moiety is optionally substituted by one or two identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino, $(C_1-C_7)$-alkylamino, di-$(C_1-C_7)$-alkylamino, carboxyl, carboxymethoxy, amino-$(C_1-C_7)$-alkyl, $(C_1-C_7)$-alkylamino-$(C_1-C_7)$-alkyl, di-$(C_1-C_7)$-alkylamino-$(C_1-C_7)$-alkyl, $(C_1-C_7)$-alkoxycarbonylmethoxy, carbamoyl, sulfamoyl, $(C_1-C_7)$-alkoxysulfonyl, sulfo- and guanidino-$(C_1-C_8)$-alkyl; or represents the radical of a 5- or 6-membered monocyclic, or 9- or 10-membered bicyclic, partially or completely hydrogenated, heteroaromatic system which has at least 1 carbon atom, 1–4 nitrogen atoms and/or 1–2 sulfur atoms and/or 1–2 oxygen atoms as ring members and is optionally mono-, di- or trisubstituted as $(C_6-C_{14})$-aryl defined under $a_1$), or $a_2$) denotes a radical of the formula VII

in which $R^{1'}$ is defined as $R^1$ under $a_1$), and W represents —CO—, —O—CO—, —SO$_2$,— —SO—, —HN—SO$_2$—, —HN—CO—, —CH(OH)— or —N(OH)—, $R^2$, $R^5$ and $R^9$ are, independently of one another, defined as $R^1$ under $a_1$), $R^3$ and $R^4$ denote, independently of one another, hydrogen or $(C_1-C_{12})$-alkyl, aryl optionally being singly or doubly unsaturated and optionally being substituted by up to 3 identical or different radicals from the series comprising hydroxyl, $(C_1-C_7)$-alkoxy, amino, mono- or di-$(C_1-C_7)$-alkylamino; or form, together with boron, X and Y, a mono-, bi- or tricyclic, saturated or partially unsaturated, mono-, di-, tri- or tetra-$(C_1-C_{12})$-alkylated ring system which as 5–18 ring members and, apart from boron, X, Y and carbon, can also contain an —O— member, an —NR$^{13}$-member or a —CR$^{14}$R$^{15}$-member X and Y, independently of one another, represent —O— or —NR$^{13}$—, $R^6$ represents hydrogen or $(C_1$∝$C_8)$-alkyl, or forms, together with $R^5$, a mono- or bicyclic, saturated or partially unsaturated ring system having 4–12 ring members, $R^7$ and $R^8$ denote, independently of one another, hydrogen; hydroxyl, amino; fluorine; amino-$(C_1-C_4)$-alkyl; hydroxy-$(C_1-C_4)$-alkyl; or $(C_1-C_4)$-alkyl which can also be singly unsaturated, $R^{10}$ and $R^{11}$ denote, independently of one another, hydrogen, hydroxyl or $(C_6-C_{14})$-aryl, aryl optionally being substituted by one or two identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino, $(C_1-C_7)$-alkylamino, di-$(C_1-C_7)$- alkylamino, carboxyl, carboxymethoxy, amino-$(C_1-C_7)$-alkyl, $(C_1-C_7)$-alkylamino-$(C_1-C_7)$-alkyl, di-$(C_1-C_7)$-alkylamino-$(C_1-C_7)$-alkyl, $(C_1-C_7)$-alkoxycarbonylmethoxy, carbamoyl, sulfamoyl, $(C_1-C_7)$-alkoxysulfonyl, sulfo- and guanidino-$(C_1-C_8)$-alkyl; or represent the radical of a 5- or 6-membered monocyclic, or 9- or 10-membered bicyclic, optionally partially or completely hydrogenated heteroaromatic system which has at least 1 carbon atom, 1-4 nitrogen atoms and/or 1-2 sulfur atoms and/or 1-2 oxygen atoms as ring members and is optionally mono- or disubstituted as $(C_6-C_{14})$-aryl above, n and m can be, independently of one another, 0, 1, 2, 3 and 4, $R^{12}$ is hydrogen or $(C_1-C_8)$-alkyl, or forms, together with $R^1$, a mono- or bicyclic, saturated or partially unsaturated ring system which has 5-12 ring members and, apart from carbon, can also contain 1 sulfur atom which can optionally be oxidized to the sulfoxide or sulfone, $A^2$ either is absent, in which case $A^1$ does not simultaneously represent a radical of the formula II, or denotes a radical which is linked N-terminal to $A^1$ and C-terminal to the amino boronic acid derivative and has the formula VIII,

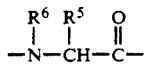

(VIII)

$R^5$ and $R^6$ being as defined above, $R^{13}$ denotes hydrogen or $(C_1-C_{12})$-alkyl which is optionally singly or doubly unsaturated and is optionally substituted by up to 3 identical or different radicals from the series comprising hydroxyl, $(C_1-C_7)$-alkoxy, amino or mono- or di-$(C_1-C_7)$-alkylamino, $R^{14}$ and $R^{15}$ denote, independently of one another, hydrogen, $(C_1-C_8)$-alkyl, hydroxymethyl, 2-hydroxyethyl, (3-hydroxysulfonyl, 2-hydroxypropyl)amino, (2-hydroxysulfonylethyl)amino, (2-hydroxysulfonylpropyl)amino, (carboxymethyl)amino, or bis(2-hydroxyethyl)amino, as well as the physiologically tolerated salts thereof, excepting the compounds Boc-Phe-Pro-[benzyl,(4,4,5,5-tetramethyl-1,3,2-dioxaborolane-2-yl)]methylamide, Box-Phe-Gly-[isobutyl,(4,4,5,5-tetramethyl-1,3,2-dioxaborolane-2-yl)]methylamide, Boc-Phe-Gly-[isobutyl,[(N-B)-(2,2'-iminodiethanolato) boryl]]methylamide, H-Phe-Gly-[isobutyl,(4,4,5,5-tetramethyl-1,3,2-dioxaborolane-2-yl)]methylamide.trifluoroacetate and Boc-D-Phe-Pro-[isopropyl,(4,4,5,5-tetramethyl-1,3,2-dioxaborolane-2-yl)]methylamide.

A radical of a 5- or 6-membered monocyclic, or 9- or 10-membered bicyclic, heteroaromatic system having at least 1 carbon atoms, 1-4 nitrogen atoms and/or 1-2 sulfur atoms and/or 1-2 oxygen atoms as ring members is to be understood to mean radicals of heteroaromatic systems as defined, for example, in Katritzky, Lagowski, Chemistry of Heterocyclic Compounds, Berlin, Heidelberg 1968. The heteroaromatic radical can be substituted by one, two or three, preferably one or two, identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino or trifluoromethyl. Examples of monocyclic heteroaromatic systems are thiophene, furan, pyrrole, imidazole, pyrazole, pyridine, pyrazine, pyrimidine, pyridazine, 1,2,4-triazole, thiazole, tetrazole, isothiazole, oxazole and isoxazole. Examples of bicyclic heteroaromatic systems are benzothiophene, benzofuran, indole, isoindole, indazole, benzimidazole, quinoline, isoquinoline, phthalazine, quinoxaline, quinazoline and cinnoline. Corresponding statements apply to radicals derived from heteroaryl, such as, for example, completely or partially hydrogenated heteroaryl, inter alia including, for example, benzodioxolane, heteroaryloxy, heteroarylthio and heteroarylalkyl.

Alkyl can be straight-chain or branched. A corresponding statement applies to radicals derived therefrom, such as for example alkoxy, alkylthio, alkylamino, dialkylamino, alkylsulfinyl, alkylsulfonyl, alkanoyl and aralkyl.

Examples of $(C_6-C_{14})$-aryl are phenyl, naphthyl, biphenylyl or fluorenyl; phenyl and naphthyl are preferred. A corresponding statement applies to radicals derived therefrom, such as, for example, aryloxy, aroyl, aralkyl and aralkyloxy. Aaralkyl is to be understood to be an unsubstituted or substituted $(C_6-C_{14})$-aryl radical which is linked to $(C_1-C_6)$-alkyl, such as, for example, benzyl, 1-and 2-naphthylmethyl, halobenzyl and akoxybenzyl, with aralkyl not, however, being restricted to the said radicals.

Salts of compounds of the formula I are to be understood to be, in particular, pharmaceutically utilizable or nontoxic salts.

Salts of these types are formed, for example, by compounds of the formula I which contain acid groups, for exampel carboxyl, with alkali metals or alkaline earth metals such as Na, K, Mg and Ca, as well as with physiologically tolerated organic amines such as, for example, triethylamine and tri(2-hydroxyethyl)amine.

Compounds of the formula I which contain basic groups, for example an amino group or a guanidino group, form salts with inorganic acids such as, for example, hydrochloric acid, sulfuric acid or phosphoric acid, and with organic carboxylic or sulfonic acids such as, for example, acetic acid, citric acid, benzoic acid, maleic acid, fumaric acid, tartaric acid and p-toluolenesulfonic acid.

Preferred compounds of the formula I are those in which the radicals are defined as follows:

$A^1$ is as defined on page 1, $R^1$ preferably denotes hydrogen, or represents $(C_1-C_{10})$-alkyl; cyclopentyl; cyclohexyl; cyclopentyl-$(C_1-C_{10})$-alkyl; cyclohexyl-$(C_1-C_{10})$-alkyl; optionally substituted phenyl-$(C_1-C_8)$-alkyl; 2-pyridyl-$(C_1-C_8)$-alkyl; 3-pyridyl-$(C_1-C_8)$-alkyl; 4-pyridyl-$(C_1-C_8)$-alkyl; $H_2N$-$(C_1-C_{10})$-alkyl; HO-$(C_1-C_{10})$-alkyl; $(C_1-C_4)$-alkoxy-$(C_1-C_{10})$-alkyl; $(C_1-C_4)$-alkoxycarbonyl-$(C_1-C_{10})$-alkyl; $(C_1-C_8)$-alkylsulfonyl; $(C_1-C_8)$-alkylsulfinyl; hydroxy-$(C_1-C_{10})$-alkanoyl such as 2-hydroxypropionyl or 2-hydroxy-3-methyl-butyryl; $(C_1-C_8)$-alkanoyloxy-$(C_1-C_{10})$-alkyl; $(C_1-C_{11})$-alkanoyl such as N-decanoyl, formyl, acetyl, propionyl, pivaloyl, isovaleryl or isobutyryl; optionally protected amino-$(C_1-C_{11})$-alkanoyl such as (3-amino,3,3-dimethyl)propionyl, 4-aminobutyryl, 5-aminopentanoyl, 6-aminohexanoyl, 4-N-tert.-butoxycarbonylaminobutyryl, 5-N-tert.-butoxycarbonylaminopentanoyl or 6-N-tert.-butoxycarbonylaminohexanoyl; di-$(C_1-C_7)$-alkylamino-$(C_2-C_{11})$-alkanoyl such as dimethylaminoacetyl; $(C_3-C_9)$-cycloalkylcarbonyl such as cyclopropylcarbonyl, cyclobutylcarbonyl, cyclopentylcarbonyl or cyclohexylcarbonyl; $(C_6-C_{10})$-aryl-$(C_2-C_{11})$-alkanoyl such as phenylacetyl, phenylpropanoyl or phenylbutanoyl; 2-pyridyl-$(C_1-C_8)$-alkanoyl; 3-pyridyl-$(C_1-C_8)$-alkanoyl; 4-pyridyl-$(C_1-C_8)$-alkanoyl; benzoyl which is optionally substituted by halogen, $(C_1-C_7)$-alkyl, ($C_1$–$C_7$)-alkoxy or ($C_1$–$C_7$)-alkoxycarbonyl, such as 4-chlorobenzoyl, 4-methylbenzoyl, 2-methoxycarbonylbenzoyl or 4-methoxybenzoyl; pyrrolyl-2-carbonyl; pyridyl-3-carbonyl; benzenesulfonyl; ($C_1$–$C_{10}$)-alkoxycarbonyl such as methoxycarbonyl, ethoxycarbonyl, isobutoxycarbonyl or tert.-butoxycarbonyl; substituted ($C_1$–$C_{10}$)-alkoxycarbonyl such as 2-(trimethylsilyl)-ethoxycarbonyl, 2,2,2-trichloroethoxy-carbonyl or 1,1-dimethyl-2,2,2-trichloroethoxycarbonyl; ($C_6$–$C_{14}$)-aryl-($C_1$–$C_6$)-alkoxycarbonyl such as benzyloxycarbonyl, 1- or 2-naphthylmethoxycarbonyl or 9-fluorenylmethoxycarbonyl; or $R^1$ forms, preferably together with $R^{12}$, a mono- or bicyclic, saturated or partially unsaturated ring system which has 5–12 ring members and, apart from carbon, can also contain 1 sulfur atom which can optionally be oxidized to the sulfoxide or sulfone, $R^2$ is preferably ($C_3$–$C_{12}$)-alkyl; mono-, bi- or tricyclic ($C_3$–$C_{18}$)-cycloalkyl, ($C_3$–$C_{18}$)-cycloalkylmethyl, ($C_3$–$C_{18}$)-cycloalkylethyl, the cycloalkyl moiety optionally being substituted by ($C_1$–$C_6$)-alkyl; dithiolanyl; ($C_6$–$C_{14}$)-arylmethyl; dithiolanylmethyl; dithiolanylethyl; dithianyl; dithianylmethyl or dithianylethyl, $R^3$ and $R^4$ are, preferably independently of one another, hydrogen or ($C_1$–$C_{12}$)alkyl or form, together with boron, X and Y, a mono-, bi- or tricyclic, saturated or partially unsaturated, optionally mono- di-, tri- or tetra-($C_1$–$C_{12}$)-alkylated ring system which has 5–18 ring members and, apart from boron, X, Y and carbon, can also contain an —O— member, an —$NR^{13}$-member or a —$CR^{14}R^{15}$-member, X and Y are, independently of one another, preferably —O— or —$NR^{13}$—, $R^5$ and $R^9$ are, indepedently of one another, preferably hydrogen; ($C_1$–$C_{10}$)-alkyl which is optionally singly or doubly unsaturated and is optionally substituted by up to 3 identical or different radicals from the series comprising hydroxyl, ($C_1$–$C_7$)-alkoxy, ($C_1$–$C_7$)-alkanoyloxy, carboxyl, ($C_1$–$C_7$)-alkoxycarbonyl, Cl, Br, amino, amidino, guanidino, carbamoyl, ($C_1$–$C_5$)-alkoxycarbonylamino, ($C_7$–$C_{15}$)-aralkoxycarbonylamino and 9-fluorenylmethoxycarbonylamino; ($C_3$–$C_{12}$)-cycloalkyl-($C_1$–$C_{13}$)-alkyl, mono- or bicyclic ($C_6$–$C_{14}$)-aryl-($C_1$–$C_3$)-alkyl which is optionally substituted by one or two identical or different radicals from the series comprising F, Cl, Br, I, hydroxyl, ($C_1$–$C_7$)-alkoxy, ($C_1$–$C_7$)-alkyl, ($C_1$–$C_7$)-alkoxycarbonyl, amino and trifluoromethyl; or preferably represent ($C_1$–$C_3$)-alkyl, substituted by the radical of a 5- or 6-membered monocyclic, or 9- or 10-membered bicyclic, optionally partially or completely hydrogenated heteroaromatic system which has at least 1 carbon atom, 1–4 nitrogen atoms and/or 1–2 sulfur atoms and/or 1–2 oxygen atoms as ring members and is optionally mono- or disubstituted as described on page 4 for ($C_6$–$C_{14}$)-aryl, $R^6$ is preferably hydrogen, methyl or ethyl or forms, together with $R^5$, preferably pyrrolidine or piperidine, each of which can also be fused with cyclopentyl, cyclohexyl or phenyl, $R^7$ and $R^8$ are, independently of one another, preferably hydrogen, hydroxyl, amino, fluorine, hydroxymethyl or aminomethyl, $R^{10}$ and $R^{11}$ are, independently of one another, preferably hydrogen, hydroxyl, phenyl, 2- or 3-thienyl, 2-, 3- or 4- pyridyl, 1-, 2- or 4-imidazolyl, 1- or 2-naphthyl or 2- or 3-benzo[b]thienyl, n and m can denote, independently of one another, 0, 1, 2, 3 and 4, $R^{12}$ is as defined on page 5, $R^{13}$ is preferably hydrogen or ($C_1$–$C_{12}$)-alkyl, $R^{14}$ and $R^{15}$ are as defined on page 5, $A^2$ is absent, in which case $A^1$ simultaneously does not represent a radical of the formula II, or denotes a radical of the formula VIII, with $R^5$ and $R^6$ being defined as on page 9.

Particularly preferred compounds of the formula I are those in which the radicals are defined as follows:

$A^1$ is as defined on page 1, $R^1$ particularly preferably denotes ($C_1$–$C_8$)-alkylsulfonyl; ($C_1$–$C_8$)-alkylsulfinyl; hydroxy-($C_1$–$C_{10}$)-alkanoyl such as 2-hydroxypropionyl or 2-hydroxy-3-methylbutyryl; ($C_1$–$C_8$)-alkanoyloxy-($C_1$–$C_{10}$)-alkyl; ($C_1$–$C_{11}$)-alkanoyl such as n-decanoyl, formyl, acetyl, propionyl, pivaloyl, isovaleryl or isobutyryl; amino-($C_1$–$C_{11}$)-alkanoyl such as (3-amino,3,3-dimethyl)propionyl, 4-aminoburyryl, 5-aminopentanoyl or 6-aminohexanoyl; di-($C_1$–$C_7$)-alylamino-($C_2$–$C_{11}$)-alkanoyl such as dimethylaminoacetyl; ($C_3$–$C_9$)-cycloalkylcarbonyl such as cyclopropylcarbonyl, cyclobutylcarbonyl, cyclopentylcarbonyl or cyclohexylcarbonyl; ($C_6$–$C_{10}$)-aryl-($C_2$–$C_{11}$)-alkanoyl such as phenylacetyl, phenylpropanoyl or phenylbutanoyl; 2-pyridyl-($C_1$–$C_8$)-alkanoyl; 3-pyridyl-($C_1$–$C_8$)-alkanoyl; 4-pyridyl-($C_1$–$C_8$)-alkanoyl; benzoyl which is optionally substituted by halogen, ($C_1$–$C_7$)-alkyl, ($C_1$–$C_7$)-alkoxy or ($C_1$–$C_7$)-alkoxycarbonyl, such as 4-chlorobenzoyl, 4-methylbenzoyl, 2-methoxyarbonylbenzoyl or 4-methoxybenzoyl; pyrrolyl-2-carbonyl; pyridyl-3-carbonyl; benzenesulfonyl; ($C_1$–$C_{10}$)-alkoxycarbonyl such as methoxycarbonyl, ethoxycarbonyl, isobutoxycarbonyl or tert.-butoxycarbonyl; substituted ($C_1$–$C_{10}$)-alkoxycarbonyl such as 2-(trimethylsilyl)-ethoxycarbonyl or 1,1-dimethyl-2,2,2-trichloroethoxycarbonyl; ($C_6$–$C_{14}$)-aryl-($C_1$–$C_6$)-alkoxycarbonyl such as benzyloxycarbonyl, 1- or 2- naphthylmethoxycarbonyl or 9-fluorenylmethoxycarbonyl, $R^2$ is particularly preferably ($C_3$–$C_{12}$)-alkyl; mono-, bi- or tricyclic ($C_3$–$C_{18}$)-cycloalkyl or ($C_3$–$C_{18}$)-cycloalkylmethyl, the cycloalkyl moiety optionally being substituted by ($C_1$–$C_4$)-alkyl; ($C_6$–$C_{14}$)-arylmethyl; dithiolanyl; dithiolanylmethyl; dithianyl and dithianylmethyl, $R^3$ and $R^4$ are particularly preferably hydrogen, or form, together with boron, X and Y, a mono-, bi or tricyclic mono-, di-, tri- or tetra-($C_1$–$C_{12}$)-alkylated, saturated or partially unsaturated ring system which has 5–18 ring members and, apart from boron, X, Y and carbon, can also contain an —O— member, an —$NR^{13}$— member or a —$CR^{14}R^{15}$-member, X and Y particularly preferably represent —O—, $R^5$ and $R^9$ are, independently of one another, particularly preferably hydrogen, methyl, ethyl, isopropyl, n-propyl, n-butyl, isobutyl, sec.-butyl, 3-guanidinopropyl, carbamoylmethyl, 2-carbamoylethyl, carboxymethyl, 2-carboxyethyl, mercaptomethyl, 2-(methylthio)ethyl, carboxyethyl, mercaptomethyl, 2-(methylthio)ethyl, (1-mercapto,1-methyl)ethyl, hydroxymethyl, 1-hydroxyethyl, amino, aminomethyl, 2-aminoethyl, 3-aminopropyl, 4-aminobutyl, N,N-dimethylamino, cyclohexylmethyl, 4-imidazolylmethyl, benzyl, 2-methylbenzyl, 3-methylbenzyl, 3-indolylmethyl, 4-hydroxybenzyl, 4-methoxybenzyl, 3,4-dihydroxybenzyl, 3,4-dimethoxybenzyl, (benzodioxolan-5-yl)methyl, 2-thienyl, 2-thienylmethyl, 2-(2-thienyl)ethyl, 3-thienyl, 3-thienylmethyl, 2-(3-thienyl)ethyl, 4-chlorobenzyl, 2-(methylsulfinyl)ethyl, 2-(methylsulfonyl)ethyl, 2- pyridylmethyl, 3-pyridylmethyl, 4-pyridylmethyl, cyclohexyl, (1-methyl-4-imidazolyl)methyl, (3-methyl-4-imidazolyl)methyl, phenyl, 1-naphthylmethyl, 2-naphthylmethyl, 2-phenylmethyl, 2-thiazolylmethyl, 4-thiazolylmethyl, 3-pyrazolylmethyl, 4-pyrimidinylmethyl, 2-indolylmethyl, 2-benzo[b]thienylmethyl, 3-benzo[b]thienylmethyl, 2-furylmethyl, $R^6$ particularly preferably denotes hydrogen or methyl or forms, together with $R^5$ and the —N—CH— group carrying these radicals, a tetrahydroisoquinoline or azabicyclooctane framework, One of the radicals $R^7$ or $R^8$ particularly preferably denotes hydrogen, and the other radical in each case denotes hydroxyl, amino, fluorine, hydroxymethyl or aminomethyl, $R^{10}$ and $R^{11}$ are, independently of one another, particularly preferably hydrogen, hydroxyl, phenyl, 2-thienyl, 2-, 3- or 4-pyridyl, 1- or 2-imidazolyl, 1-naphthyl, or 2- or 3-benzo[b]thienyl, n and m are, independently of one another, particularly preferably 0, 1 or 2, $R^{12}$ is particularly preferably hydrogen or methyl or forms, together with $R^1$, a mono- or bicyclic saturated or partially unsaturated ring system which has 5–12 ring members and, apart from carbon, can also contain 1 sulfur atom which can optionally be oxidized to the sulfoxide or sulfone, $R^{13}$ is particularly preferably hydrogen or $(C_1-C_4)$-alkyl, $R^{14}$ and $R^{15}$ are as defined on page 5, $A^2$ is absent, in which case $A^1$ does not simultaneously represent a radical of the formula LI, or denotes a radical of the formula VIII, with $R^5$ and $R^6$ being defined as on pages 3 and 4.

Further particularly preferred compounds of the formula I are those in which $A^1$ represents a radical of the formula II, III or VI in which $R^1$ denotes $(C_1-C_6)$-alkylsulfonyl such as, for example, ethylsulfonyl, isopropylsulfonyl, isobutylsulfonyl, sec.-butylsulfonyl or tert.-butylsulfonyl; $(C_1-C_6)$-alkylsulfinyl, such as, for example, ethylsulfinyl, isopropylsulfinyl, isobutylsulfinyl, sec.-butylsulfinyl or tert.-butylsulfinyl; $(C_1-C_6)$-alkanoyl, such as, for example, acetyl, propionyl, isobutyryl, isovaleryl or pivaloyl; Amino-$(C_1-C_6)$-alkanoyl, such as, for example, (3-amino,3,3-dimethyl)propionyl; $(C_1-C_60)$-alkoxycarbonyl such as, for example, ethoxycarbonyl, isobutoxycarbonyl or tert.-butoxyarbontyl; $(C_6-C_{10})$-aryl-$(C_1-C_6)$-alkoxycarbonyl, such as, for example, benzyloxycarbonyl, 1- or 2-naphthylmethoxycarbonyl, $R^2$ denotes $(C_5-C_8)$-cycloalkyl; $(C_5-C_{11})$-cycloalkylmethyl; [$(C_1-C_4)$-alkyl-cyclohexyl]methyl; $(C_3-C_4)$-alkyl, which is substituted by $(C_1-C_3)$-alkyl; $(C_6-C_{10})$-arylmethyl or dithiolan-2-yl-methyl, $R^3$ and $R^4$ represent hydrogen, or form, together with boron, X and Y, a 1,3,2-dioxaborolane radical which is optionally substituted by 1 to 4 methyl groups, a [4,5-diisopropyl]-1,3,2-dioxaborolane, a [(N-B)-(2,2'-iminodiethanolato)-boryl)], a pinandioxyboryl or a 1,3,2-dioxaborinane radical whose carbon atom in position 5 is substituted by $R^{14}$ and $R^{15}$, X and Y preferably represent —O—, $R^5$ denotes hydrogen, n-propyl, isopropyl, n-butyl, isobutyl, sec.-butyl, carbamoylmethyl, 2-carbamoylethyl, benzyl, 2-methylbenzyl, 3-methylbenzyl, 2-thienylmethyl, 3-thienylmethyl, 1-naphthylmethyl, 2-naphthylmethyl, imidazol-4-yl-methyl or 2-thiazolylmethyl, $R^6$ represents hydrogen or methyl, $R^{10}$ and $R^{11}$ denote, independently of one another, 1-naphthyl or 2-thienyl, n and m represent 1, $R^{12}$ denotes hydrogen, $R^{14}$ and $R^{15}$ denote, independently of one another, hydrogen, $(C_1-C_8)$-alkyl, hydroxymethyl, 2-hydroxyethyl, (3-hydroxysulfonyl, 2-hydroxypropyl)-amino (2-hydroxysulfonylethyl)amino, (2-hydroxysulfonylpropyl)amino, (carboxymethyl)amino or bis(2-hydroxyethyl)amino, and $A^2$ represents a radical of the formula VIII, with $R^5$ and $R^6$ being defined as on pages 11 and 12. The invention also relates to a process for the preparation of compounds of the formula I, which comprises coupling a fragment having a terminal carboxyl group, or a reactive derivative thereof, with a corresponding fragment having a free amino group, where appropriate eliminating (a) protective group(s) which has (have) been temporarily introduced to protect other functional groups, and where appropriate converting the compound obtained in this way into its physiologically tolerated salt.

Fragments of a compound of the formula I having a terminal carboxyl group have the formulae IX to XI which follow $A^1—OH$          (IX)

$A^1—A^2—OH$      (X)

Fragments of a compound of the formula I having a terminal amino group have the formulae XI to XIV which follow

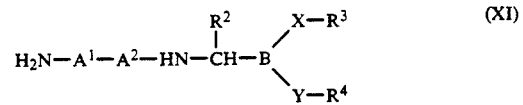
(XI)

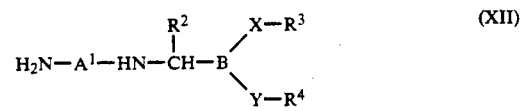
(XII)

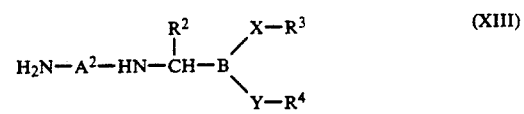
(XIII)

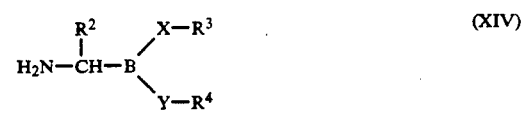
(XIV)

Methods suitable for the preparation of an amide bond are described in, for example, Houben-Weyl, Methoden der organischen Chemie (Methods of organic chemistry) Volume 15/2; Bodanszky et al., Peptide synthesis, 2nd ed. (Wiley & Sons, N.Y. 1976) or Gross, Meienhofer, The peptides: analysis, synthesis, biology (Academic Press, N.Y. 1979). The following methods are preferably used: active ester method using N-hydroxysuccinimide, 1-hydroxybenzotriazole or 3-hydroxy-4-oxo-3,4-dihydro-1,2,3-benzotriazine as alcohol component, coupling with a carbodiimide such as dicyclohexylcarbodiimide or with propanephosphonic anhydride, and the mixed anhydride method using pivaloyl chloride or ethyl or isobutyl chloroformate.

Fragments of the formula IX which a) are covered by formula II are synthesized by the generally known methods for the preparation of amino acids;

b) are covered by the formula III are synthesized starting from the corresponding amino acids, retaining the chirality center thereof. Diazotization at $-20°$ C. to $50°$ C. in dilute mineral acids results in $\alpha$-bromo carboxylic acids or, via the lactic acids, in $\alpha$-trifluoromethanesulfonyloxy carboxylic acids, each of which can be reacted with a nucleophile carrying $R^1$ and $R^{12}$;

c) are covered by formula VI are synthesized starting from amino aldehydes, which are prepared by the method of B. Castro et al. (Synthesis 1983, 676). Wittig reaction with methyltriphenylphosphonium bromide under the generally known conditions, followed by epoxidation with m-chloroperbenzoic acid provides N-protected amino epoxides. Opening with trimethylsilyl chloride/NaI in acetonitrile in the temperature range from $-20°$ C. to the boiling point of the solvent, desilylation with CsF and acetonation with 2,2-dimethoxypropane/p-toluenesulfonic acid at $0°$ C. to $110°$ C. provides a protected iodide. The latter is either reacted directly with ester enolates under the generally known conditions of C-alkylation of ester enolates or, if higher reactivity is desired, converted via the formate (prepared with sodium formate in a dipolar aprotic solvent at $60°$ C. to $150°$ C.) and the alcohol into the trifluoromethanesulfonate. It is also possible to react this electrophile with ester enolates which, by reason of steric hinderance in $R^9$, cannot be reacted with iodide as described above;

d) are covered by formula V are prepared starting from the corresponding carboxylic acid by reaction with a radical of the formula III and, after conversion into the aldehydes, reacted further as described under c);

e) are covered by formula VI are prepared starting from malonic esters whose alkylation with arylalkyl halides provides mono- or disubstituted malonic esters which, after hydrolysis, are converted into the desired derivatives by decarboxylation. In the case where one of the radicals $R^{10}$ or $R^{11}$ denotes hydroxyl, preparation starts from the corresponding amino acid and, after diazotization (as described above), the lactic acid is obtained (number of $CH_2$ groups carrying $R^{10}$ or $R^{11}=0$), or from the substituted malonic acid, in which case monohydrolysis and selective reduction (with, for example, diborane or $LiAlH_4$) yields the 2-substituted 3-hydroxypropionic acid.

The amino boronic acid derivatives of the formula I are prepared starting from trialkyl borates such as, for example, $B(OMe)_3$, $B(OEt)_3$, $B(OiPr)_3$, $B(OnBu)_3$ or $B(OtBu)_3$. $R^2$ is introduced by a Grignard reaction at temperatures between $-100°$ C. and $+50°$ C., preferably between $-78°$ C. and $0°$ C., in a solvent which is insert to organometallic reagents, such as ethers, for example diethyl ether, tetrahydrofuran or dimethoxyethane. It is also possible to use corresponding alkyllithium or aryllithium compounds to introduce $R^2$ under the same reaction conditions. It is then expedient to carry out conversion into a relatively hydrolysis-resistant boronic ester such as the pinacol ester or, if asymmetric synthesis is intended, into the pinanediol ester of desired stereochemistry or the 1,2-diisopropylethanediol ester. This is best carried out with acid catalysis and removal of the lower alkyl alcohol under reduced pressure. The boronic esters are then reacted with $LiCHCl_2$ at $-120°$ C. to $-70°$ C., preferably at $-110°$ C. to $-90°$ C., in a solvent such as diethyl ether or tetrahydrofuran. The initial product is the dichloromethyl boronate which finally rearranges at room temperature, with elimination of $Cl^-$, to give the boronic ester which has been extended by one $-CHCl-$ group. To increase the reactivity, chlorine is then replaced by iodine by reaction with NaI in acetonitrile at $0°$ C. to $50°$ C. Reaction thereof with lithium bis(trimethylsilyl)amide at $0°$ C. to $50°$ C. in a solvent which is inert to strong bases, such as in ethers, followed by desilylation of the product in trifluoroacetic acid provides the substituted $\alpha$-amino boronic esters as crystallizing trifluoroacetic acid salts. The latter can be reacted, in analogy to peptide coupling, with amino carboxylic esters with the $A^1$-OH or $A^2$-$A^2$-OH residues.

The preceding and subsequent operations necessary for the preparation of compounds of the formula I, such as introduction and elimination of protective groups, are known from the literate and described, for example, in T. W. Greene "Protective groups in organic synthesis" (John Wiley & Sons, N.Y. 1981). Salts of compounds of the formula I with salt-forming groups are prepared in a manner known per se, for example by reacting a compound of the formula I having a basic group with a stochiometric amount of a suitable acid. Stereoisomeric mixtures, in particular diastereomeric mixtures which result, where appropriate, in the synthesis of compounds of the formula I, can be separated in a manner known per se by fractional crystallization or by chromatography.

The compounds of the formula I according to the invention have enzyme-inhibitory properties; in particular, they inhibit the action of the natural enzyme renin. Renin is a proteolytic enzyme which belongs to the aspartyl protease class and which is secreted, following various stimuli (volume depletion, sodium deficiency, $\beta$-receptor stimulation), from the juxtaglomerular cells of the kidney into the circulating blood. There it cleaves the decapeptide angiotensin I off the angiotensinogen which is secreted from the liver. The former is converted by angiotensin converting enzyme (ACE) into angiotensin II. Angiotensin II plays a considerable part in the regulation of blood pressure because it increases the blood pressure directly by vasoconstriction. In addition, it stimulates the secretion of aldosterone from the adrenal, and in this way increases, via the inhibition of sodium excretion, the extracellular fluid volume, which, in turn, contributes to increasing the blood pressure. Inhibitors of the enzymatic activity of renin bring about a decrease in the formation of angiotensin I, which results in a decrease in the formation of angiotensin II. The lowering of the concentration of the latter active peptide hormone is the direct reason why renin inhibitors act to lower the blood pressure.

The activity of renin inhibitors can be checked by in vitro tests. These entail the decrease in the formation of angiotensin I being measured in various systems (human plasma, purified human renin).

1. Principle of the Test

For example human plasma which contains both renin and angiotensinogen is incubated at $37°$ C. with the compound to be tested. During this, angiotensin I is liberated from angiotensinogen under the action of renin and can subsequently be measured using a commercially available radioimmunoassay. This liberation of angiotensin is inhibited by renin inhibitors.

2. Obtaining the Plasma

The blood is obtained from volunteer subjects (about 0.5 litre per person; Bluko sampler from ASID Bonz and Sohn, Unterschleissheim) and is collected in partially evacuated bottles while cooling in ice. Coagulation is prevented by addition of EDTA (final concentration 10 mM). After centrifugation, (HS 4 Rotor (Sorvall), 3500 rpm, 0°–4° C., 15 min; repeat if necessary), the plasma is carefully removed with a pipette and frozen in suitable portions at $-30°$ C. Only plasma with sufficiently high renin activity are used for the test. Plasma with low renin activity are activated by cold treatment ($-4°$ C., 3 days (prorenin→renin).

4.(sic) Test Procedure

Angiotensin I is determined using the Renin-Maia ® Kit (Serono Diagnostics S. A., Coinsins, Switzerland). The plasma is incubated in accordance with the instructions given therein:

| Incubation mixture: | 1000 μl of plasma (defrozen at 0–4° C.) |
|---|---|
| | 100 μl of phosphate buffer (ph 7.4) addition of $10^{-4}$M Ramiprilate) |
| | 10 μl of PMSF solution |
| | 10 μl of 0.1% Genapol PFIC |
| | 12 μl of DMSO or test product |

The test products are generally dissolved $10^{-2}$ M in 100% dimethylsulfoxide (DMSO) and diluted appropriately with DMSO; the incubation mixture contains not more than 1% DMSO.

The mixtures are mixed up in ice and placed in a water bath (37° C.) for 1 hour for the incubation. 6 samples in total (each of 100 μl) are taken from an additional mixture without inhibitor and without further incubation for the determination of the initial angiotensin I content of the plasma used.

The concentrations of the test products are selected such that the 10–90% range of enzyme inhibition is approximately covered (at least five concentrations). At the end of the incubation time, three 100 μl samples from each mixture are frozen in precooled Eppendorf tubes on dry ice and stored at about $-25°$ C. for the determination of angiotensin I (means from three individual samples).

Angiotensin I Radioimmunoassay (RIA)

The instructions for use of the RIA Kit (Rennin-Maia ® Kit, Serono Diagnostics S. A., Coinsins, Switzerland) are followed exactly.

The calibration plot embraces the range from 0.2 to 25.0 ng of angiotensin I per ml. The basic angiotensin I content of the plasma is subtracted from all the measured values. The plasma renin activity (PRA) is reported as ng of Ang I/ml x hour. PRA values in the presence of the test substances are related to a mixture without inhibitor (=100%) and reported as % residual activity. The $IC_{50}$ value is read off from the plot of % residual activity against the concentration (M) of the test product (logarithmic scale).

The compounds of the general formula I described in the present invention show, in the in vitro test, inhibitory effects at concentrations of about $10^{-5}$ to $10^{-10}$ mol/l. The values determined are detailed below:

TABLE 1

| Example No. | $IC_{50}[M]$ human plasma renin |
|---|---|
| 1 | $4.2 \cdot 10^{-7}$ |
| 2 | $1.0 \cdot 10^{-6}$ |
| 3 | $2.0 \cdot 10^{-6}$ |
| 4 | $4.5 \cdot 10^{-7}$ |
| 5 | $5.5 \cdot 10^{-7}$ |
| 7 | $6.7 \cdot 10^{-7}$ |
| 8 | $6.5 \cdot 10^{-7}$ |
| 9 | $2.7 \cdot 10^{-7}$ |
| 13 | $2.4 \cdot 10^{-6}$ |
| 15 | $2.8 \cdot 10^{-6}$ |
| 16 | $3.0 \cdot 10^{-6}$ |
| 18 | $9.0 \cdot 10^{-6}$ |
| 19 | $8.0 \cdot 10^{-6}$ |
| 22 | $7.3 \cdot 10^{-6}$ |
| 23 | $7.8 \cdot 10^{-6}$ |
| 29 | $4.4 \cdot 10^{-6}$ |
| 30 | $1.7 \cdot 10^{-6}$ |
| 31 | $3.3 \cdot 10^{-7}$ |
| 32 | $5.0 \cdot 10^{-7}$ |
| 33 | $5.0 \cdot 10^{-6}$ |
| 34 | $3.0 \cdot 10^{-6}$ |
| 35 | $2.8 \cdot 10^{-7}$ |
| 36 | $6.2 \cdot 10^{-7}$ |
| 39 | $2.1 \cdot 10^{-6}$ |
| 40 | $3.6 \cdot 10^{-6}$ |
| 41 | $1.5 \cdot 10^{-6}$ |
| 42 | $9.5 \cdot 10^{-7}$ |
| 43 | $5.5 \cdot 10^{-7}$ |
| 44 | $2.4 \cdot 10^{-6}$ |
| 50 | $1.5 \cdot 10^{-6}$ |
| 51 | $1.8 \cdot 10^{-6}$ |
| 52 | $2.8 \cdot 10^{-6}$ |
| 54 | $9.0 \cdot 10^{-7}$ |

Renin inhibitors bring about a lowering of blood prsesure in salt-depleted animals. Since human renin differs from the renin of other species, primates such as, for example, Rhesus monkeys are used for the in vivo test of renin inhibitors. Primate renin and human renin are substantially homologous in their sequence. Endogenous renin release is stimulated by i.v. injection of furosemide. The test compounds are then administered by continuous infusion, and their effect on blood pressure and heart rate is measured. In this test, the compounds of the present invention are active in a dose range of about 0.1–5 mg/kg i.v., and in the dose range of about 1–50 mg/kg in intraduodenal administration by gastroscope. The compounds of the general formula I described in the present invention can be used as antihypertensive agents and for the treatment of cardiac insufficiency.

Hence the invention also relates to the use of compounds of the formula I as medicines, and to pharmaceutical products which contain these compounds. Administration to primates, especially to humans, is preferred.

Pharmaceutical products contain an effective amount of the active substance of the formula I together with an inorganic or organic pharmaceutically utilizable vehicle. Administration can be intranasally, intravenously, subcutaneously, orally or intraduodenally. The dosage of the active substance depends on the warm-blooded species, the body weight, age, and mode of administration.

The pharmaceutical products of the present invention are prepared in dissolving, mixing, granulating or coating processes known per se.

For the form for oral administration, the active compounds are mixed with the additives customary for this purpose, such as vehicles, stabilizers or inert diluents, and converted by customary methods into suitable dosage forms, such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose, magnesium stearylfumarate or starch, especially corn starch. In this connection, preparation can be carried out both as dry and wet granules. Examples of suitable oily vehicles or solvents are vegetable or animal oils, such as sunflower oil and fish liver oil.

For subcutaneous or intravenous administration, the active compounds, or physiologically tolerated salts thereof, are converted into solutions, suspensions or emulsions, if desired with the substances customary for this purpose, such as solubilizers, emulsifiers or other auxiliaries. Examples of suitable solvents are: water, physiological saline solutions, or alcohols for example ethanol, propandiol or glycerol, as well as sugar solutions such as glucose or mannitol solutions, or a mixture of the various solvents mentioned.

List of Abbreviations Used:

| | |
|---|---|
| Ac | acetyl |
| Boc | tert.butoxycarbonyl |
| BuLi | n-butyllithium |
| TLC | thin-layer chromatography |
| DCC | dicyclohexylcarbodiimide |
| DCI | desorption chemical ionization |
| DIP | diisopropyl ether |
| DNP | 2,4-dinitrophenyl |
| DMF | dimethylformamide |
| DMSO | dimethyl sulfoxide |
| EA | ethyl acetate |
| EI | electron impact |
| Etoc | ethoxycarbonyl |
| FAB | fast atom bombardment |
| H | hexane |
| HOBt | 1-hydroxybenzotriazole |
| Iva | isovaleryl |
| M | molecular peak |
| MeOH | methanol |
| MS | mass spectrum |
| MTB | methyl tert.-butyl ether |
| Nva | norvaline |
| Nle | norleucine |
| R.T. | room temperature |
| M.P. | melting point |
| B.P.$_{xx}$ | boiling point at xx torr |
| Thi | β-2-thienylalanine |
| THF | tetrahydrofuran |
| Z | benzyloxycarbonyl |

The other abbreviations used for amino acids correspond to the three-letter code customary in peptide chemistry, as described in, for example, Europ. J. Biochem. 138, 9–37 (1984). Unless expressly indicated otherwise, the amino acids are always of the L configuration.

The examples which follow serve to illustrate the present invention without intending to restrict it to them.

EXAMPLE 1

Iva-Phe-Nva-[cyclohexylmethyl,(4,4,5,5-tetramethyl-1,3,2-dioxaborolane-2-yl)]methylamide 139 mg of Iva-Phe-Nva-Oh are dissolved in 5 ml of THF and, at −20° C., first 44 µl of N-methylmorpholine and then 52 µl of isobutyl chloroformate are injected. After 5 minutes at −20° C. 56 µl of triethylamine in 2 ml of THF are added. The mixed anhydride obtained in this way is injected, at −20° C., into a solution of 2[(1′-amino-2′-cyclohexyl)ethyl],4,4,5,5-tetramethyl-1,3,2-dioxaborolane (trifluoracetic acid salt) in 5 ml of THF, the mixture is stirred at −20° C. for 1 h and at R.T. for a further 2 h, THF is removed in vacuo, and the residue is taken up in 20 ml of ethyl acetate. The solution is extracted twice with 20 ml of saturated aqueous NaHCO$_3$ and twice with 20 ml of 0.06M KH$_2$PO$_4$. It is then dried over Na$_2$SO$_4$ and the solvent is removed in vacuo, and the residue is chromatographed on silica gel with MTB. 105 mg of the title compound are obtained as a colorless amorphous powder.

R$_f$(MTB) = 0.38    MS(FAB): 584(M + 1)

a)

2-[(1′-amino-2′-cyclohexyl)ethyl],4,4,5,5-tetramethyl-1,3,2-dioxaborolane(trifluoracetic acid salt)

0.7 ml of hexamethyldisilazane are dissolved in 8 ml of THF and, at −78° C., 2.1 ml of 1.6M BuLi in hexane are added. The mixture is left to stir at R.T. for 5 minutes, again cooled to −78° C., and 1.1 g of 2-[(1′-iodo-2′-cyclohexyl) ethyl], 4,4,5,5-tetramethyl-1,3,2-dioxaborolane in 5 ml of THF are added. The mixture is stirred at R.T. for 22 h, then the THF is removed in vacuo and the residue is taken up in 4 ml of diethyl ether. Then, at 0° C., 0.3 ml of trifluoroacetic acid is slowly added dropwise, and the mixture is stirred at this temperature for 10 minutes, during which a white crystalline precipitate separates out. The latter is filtered off under an argon atmosphere and washed with diethyl ether which has been cooled to 0° C. 650 mg of the title compound are obtained as white crystals.

M.P. 154–157° C.    MS(DCI): 254(M + 1)

b)

2-[(1′-iodo-2′-cyclohexyl)ethyl],4,4,5,5-tetramethyl-1,3,2-dioxaborolane 3.6 g of NaI are dissolved in 50 ml of acetonitrile, and 4.3 mg of 2-[(1′-chloro-2′-cyclcohexyl)ethyl],4,4,5,5-tetramethyl-1,3,2-dioxaborolane dissolved in 20 ml of acetonitrile are added dropwise at R.T. NaCl starts to separate out after about 5 minutes. After the solution has been stirred at R.T. for 3 hours, it is filtered, the acetonitrile is removed in vacuo, and the residue is chromatographed on silica gel with MTB/H 1:10. 4.4 g of the title compound are obtained as a pale yellow oil.

R$_f$(EA/H 1:8) = 0.59    MS(EI): 364(M)

c)

2-[(1′-chloro-2′-cyclohexyl)ethyl],4,4,5,5-tetramethyl-1,3,2-dioxaborolane 6.8 g of CH$_2$Cl$_2$ are dissolved in 80 ml of THF and cooled to −100° C. 31.3 ml of 1.6M BuLi which have been precooled to −78° C. are now added dropwise sufficiently slowly for the temperature in the reaction flask not to rise above −95° C. Then 11.2 g of 2-cyclohexylmethyl,-4,4,5,5-tetramethyl-1,3,2-dioxaborolane in 25 ml of diethyl ether which have been precooled to −78° C. are run in. The solution is then stirred at R.T. for 20 h and stirred into 300 ml of phosphate buffer (ph=7), the mixture is extracted 3 times with 200 ml of MTB each time, the organic phase is dried over $Na_2SO_4$, the solvent is removed in vacuo, and the residue is chromatographed on silica gel with EA/H 1:8. 5.3 g of the title compound are obtained as a colorless oil.

$R_f$(EA/H 1:8) = 0.50   MS(EI): 272(M)

d) 2-cyclohexylmethyl,4,4,5,5-tetramethyl-1,3,2-dioxaborolane 62.9 ml of cyclohexylmethyl bromide are slowly added dropwise to 12.0 g of magnesium and 200 ml of diethyl ether. After the magnesium has dissolved, the solution of the Grignard compound is added dropwise to a solution of 50.3 ml of trimethyl borate in 100 ml of diethyl ether which has been precooled to −78° C. in such a way that the temperature does not rise above −55° C., and the mixture is then stirred at R.T. for 2 h. Then, while cooling in ice, 113 ml of 40% strength $H_2SO_4$ are added in such a way that the internal temperature does not rise above 25° C. 53.2 g of pinacol in 100 ml of diethyl ether are now poured in, and the diethyl ether together with the biproduct methanol are removed in a rotary evaporator. The pH is then adjusted with $NaHCO_3$ to 8, the mixture is extracted 3 times with 200 ml of MTB, the organic phase is dried over $Na_2SO_4$, the solvent is removed in vacuo, and the residue is distilled under high vacuum. 49.7 g of the title compound are obtained as a colorless oil.

$B.P._{0.05}$ = 57° C.   MS(EI): 224(M)

The compound of Example 2 is prepared in analogy to Example 1.

EXAMPLE 2

Iva-Phe-Nle-[cyclohexylmethyl,(4,4,5,5-tetramethyl-1,3,2-dioxaborolane-2-yl)]methylamide $R_f$(MTB) = 0.46   MS(FAB): 598(M + 1)

EXAMPLE 3

Iva-Phe-His-[cyclohexylmethyl,(4,4,5,5-tetramethyl-1,3,2-dioxaborolane-2-yl)]methylamide 230 mg of Iva-Phe-His(DNP)-]cyclohexylmethyl,(4,4,5,5-tetramethyl-1,3,2-dioxaborolane-2-yl)]methylamide are dissolved in 5 ml of acetonitrile, and 39 ml of thiophenol are added. The mixture is stirred at R.T. for 2 h, and then the solvent is removed in vacuo and the residue is chromatographed on silica gel with acetone. 65 mg of the title compound are obtained as a colorless resin.

$R_f$(acetone) = 0.58   MS(FAB): 622(M + 1)

a) Iva-Phe-His(DNP)-[cyclohexylmethyl,(4,4,5,5-tetramethyl-1,3,2-dioxaborolane-2-yl)]methylamide is prepared in analogy to Example 1.

The compound of Example 4 is prepared in analogy to Example 3.

EXAMPLE 4

Iva-Thi-His-[cyclohexylmethyl,(4,4,5,5-tetramethyl-1,3,2-dioxaborolane-2-yl)]methylamide $R_f$(MTB) = 0.48   MS(FAB): 628(M + 1)

EXAMPLE 5

Iva-Phe-Nva-(cyclohexylmethyl,dihydroxyboryl)methylamide 0.86 ml of a 0.5M solution of $BCl_3$ in $CH_2Cl_2$ is cooled to −78° C., and 100 mg of the title compound from Example 1 in 0.86 ml of $CH_2CH_2$ are slowly added dropwise. The mixture is then stirred at 0° C. for 1 h and poured into 10 ml of 0.1 N NaOH and the mixture is washed twice with 10 ml of EA. The aqueous phase is then acidified to about pH 2 with HCl and is extracted 3 times with 10 ml of EA, the organic phase is dried over $Na_2SO_4$, the solvent is removed in vacuo, and the residue is chromatographed on silica gel with acetone/water 10:1. 20 mg of the title compound are obtained as a colorless foam.

$R_f$(acetone/$H_2O$ 10:1) = 0.45–0.60   MS(FAB, glycerol matrix): 557(M + 56)

EXAMPLE 6

Iva-Phe-Nva-[cyclohexylmethyl,[(N-B)-(2,2'-iminodiethanolato)-boryl]]methylamide 74 mg of the title compound from Example 1 are suspended in 5 ml of EA. Then 12.2 μl of diethanolamine are added, and the mixture is agitated in an ultrasonic bath at R.T. for 5 h. The solvent is removed in vacuo, and the $CH_2Cl_2$-soluble part of the reaction mixture is chromatographed on silica gel with MTB/H 5:1. 7 mg of the title compound are obtained as an amorphous powder.

$R_f$(MTB)=0.37.

The column is then eluted with acetone/water 10:1, and 41 mg of the title compound of Example 5 are obtained.

The compound of Example 7 is prepared in analogy to Example 1.

EXAMPLE 7

Iva-Phe-Thi-[cyclohexylmethyl,(4,4,5,5-tetramethyl-1,3,2-dioxaborolane-2-yl)]methylamide $R_f$(MTB) = 0.50   MS(FAB): 638(M + 1)

EXAMPLE 8

Iva-Phe-Thi-(cyclohexylmethyl,dihydroxyboryl)methylamide 165 mg of the title compound from Example 7 are dissolved in 5 ml of EA, and 25 μl of diethanolamine are added. The mixture is agitated in an ultrasonic bath at R.T. for 5 h, during which the diethanolamine ester of the title compound separates out. The solvent is removed in vacuo, and the residue is chromatographed on silica gel with acetone/$H_2O$=10:1. 62 mg of the title compound are obtained as a colorless foam.

$R_f$(acetone/$H_2O$ 10:1)=0.45–0.55.

MS (FAB, glycerol matrix):611 (M+56).

The compound of Example 9 is prepared in analogy to Example 8 from the title compound of Example 4.

EXAMPLE 9

Iva-Thi-His-(cyclohexylmethyl,dihydroxyboryl)methylamide $R_f$(acetone/H$_2$) 10:1)=0.10.
MS (FAB, glycerol matrix):601 (M+56).

The compounds of Examples 10 and 11 are prepared in analogy to Example 1.

EXAMPLE 10

Iva-Phe-Nva-[(naphthylmethyl),(4,4,5,5-tetramethyl-1,3,2-dioxaborolane-2-yl)]methylamide $R_f$(MTB) = 0.45    MS(FAB): 628(M + 1)

EXAMPLE 11

Iva-Phe-Nva-[cyclooctylmethyl,(4,4,5,5-tetramethyl-1,3,2-dioxaborolane-2-yl)]methylamide $R_f$(MTB) = 0.43    MS(FAB): 612(M + 1)

The compound of Example 12 is prepared in analogy to Example 8 from the title compound of Example 11.

EXAMPLE 12

Iva-Phe-Nva-(cyclooctylmethyl,dihydroxyboryl)methylamide $R_f$(acetone/H$_2$O 10:1)=0.55–0.65.
MS (FAB, glycerol matrix): 585 (M+56).

The compounds of Examples 13–17 are prepared to analogy to Example 1:

EXAMPLE 13

Iva-Phe-Nva-[cyclohexylmethyl,(-)-pinanedioxyboryl]-methylamide $R_f$(EA/H 1:1) = 0.19    MS(FAB): 636(M + 1)

EXAMPLE 14

Iva-Phe-Nva-[cycloundecylmethyl,(4,4,5,5-tetramethyl-1,3,2-dioxaborolane-2-yl)]methylamide $R_f$(MTB) = 0.50    MS(FAB): 550(M + 1)

EXAMPLE 15

Iva-Phe-Nva-[(4-methylcyclohexyl)methyl,(4,4,5,5-tetramethyl-1,3,2-dioxaborolane-2-yl)]methylamide $R_f$(EA/H 1:1) = 0.10    MS(FAB): 598(M + 1)

EXAMPLE 16

Iva-Phe-Nva-[(cycloheptylmethyl,(4,4,5,5-tetramethyl-1,3,2-dioxaborolane-2-yl)]methylamide $R_f$(MTB) = 0.35    MS(FAB): 598(M + 1)

EXAMPLE 17

Iva-Phe-(N-Me-Phe)-[cyclohexylmethyl,(4,4,5,5-tetramethyl-1,3,2-dioxaborolane-2-yl)]methylamide $R_f$(DIP/MTB 1:1) = 0.20    MS(FAB): 646(M + 1)

The compounds of examples 18–20 are prepared in analogy to example 3:

EXAMPLE 18

Iva-Phe-His-[cycloctylmethyl,(4,4,5,5-tetramethyl-1,3,2-dioxaborolane-2-yl)]methylamide $R_f$(acetone) = 0.10    MS(FAB: 650(M + 1)

EXAMPLE 19

Iva-Phe-His-[cycloheptylmethyl,(4,4,5,5-tetramethyl-1,3,2-dioxaborolane-2-yl)]methylamide $R_f$(acetone) = 0.12    MS(FAB): 634(M + 1)

EXAMPLE 20

Bis-(1-napthylmethyl)acetyl-His-[3-methyl,1-(4,4,5,5-tetramethyl-1,3,2-dioxaborolane-2-yl)]butylamide $R_f$(acetone) = 0.20    MS(FAB): 673(M + 1)

The compounds of examples 21–34 are prepared from the corresponding 1,3,2-dioxaborolanes in analogy to example 8.

EXAMPLE 21

Iva-Phe-Nva-(cyclooctylmethyl,dihydroxyboryl)methylamide $R_f$(acetone/H$_2$O 10:1)=0.54.
MS (FAB, glycerol): 586 (M+57).

EXAMPLE 22

Iva-Phe-Nva-(cycloheptylmethyl,dihydroxyboryl)methylamide $R_f$ (acetone/H$_2$O 10:1)=0.47; MS (FAB, glycerol): 572 (M+57).

EXAMPLE 23

Iva-Phe-Nva-[(4-methylcyclohexyl)methyl,dihydroxyboryl]-methylamide $R_f$(acetone/H$_2$O 10:1)=0.57.
MS (FAB, glycerol): 572 (M+57).

EXAMPLE 24

Iva-Phe-His-(cycloheptylmethyl,dihydroxyboryl)methylamide $R_f$(acetone/H$_2$O 10:1)=0.14.
MS (FAB, glycerol): 610 (M+57).

EXAMPLE 25

Iva-Phe-His-(cyclooctylmethyl,dihydroxyboryl)methylamide $R_f$(acetone/H$_2$O 5:1)=0.29.
MS (FAB, glycerol): 624 (M+57).

EXAMPLE 26

Iva-Phe-Nva-(cycloundecylmethyl,dihydroxyboryl)-methylamide $R_f$(acetone/H$_2$O 15:1)=0.45.
MS (FAB, glycerol): 628 (M+57).

EXAMPLE 27

(3-t-Butylsulfonyl)propionyl-Nva-(cycloundecylmethyl, dihydroxyboryl)methylamide $R_f$(acetone/H$_2$O 10:1)=0.57.
MS (FAB, glycerol): 573 (M+57).

EXAMPLE 20

(3-t-Butylsulfonyl)propionyl-Nva-(1-naphthylmethyl, dihydroxyboryl)methylamide $R_f$(acetone/H$_2$O 10:1)=0.29.
MS (FAB, glycerol): 547 (M+57).

EXAMPLE 29

(2-Benzyl,3-t-butylsulfonyl)propionyl-Val-(cyclohexylmethyl, dihydroxyboryl)methylamide $R_f$(acetone/H$_2$O 10:1)=0.57.
MS (FAB, glycerol): 593 (M+57).

EXAMPLE 30

[3-t-Butylsulfonyl,2-(2-thienylmethyl)]propionyl-Nva-(cycloheptylmethyl,dihydroxyboryl)methylamide $R_f$(acetone/H$_2$O 10:1)=0.55.
MS (FAB, glycerol): 613 (M+57).

EXAMPLE 31

(3-t-Butylsulfonyl,2-(2-thienylmethyl)]propionyl-Nva-(cyclohexylmethyl,dihydroxyboryl)methylamide $R_f$(acetone/H$_2$O 10:1)=0.44.
MS (FAB, glycerol): 599 (M+57).

EXAMPLE 32

[3-t-Butylsulfonyl,2-(2-thienylmethyl)]propionyl-Thi-(cyclohexylmethyl, dihydroxyboryl)methylamide $R_f$(acetone/H$_2$O 20:1)=0.35.
MS (FAB, glycerol): 653 (M+57).

EXAMPLE 33

(2-Benzyl,3-t-butylsulfonyl)propionyl-Nva-(cyclopentylmethyl,dihydroxyboryl)methylamide $R_f$(acetone/H$_2$O 10:1)=0.41.
MS (FAB, glycerol): 579 (M+57).

EXAMPLE 34

[8-t-Butylsulfonyl,2-(2-thienylmethyl)]propionyl-Thi-(cycloheptylmethyl,dihydroxyboryl)methylamide $R_f$(acetone/H$_2$O 10:1)=0.60.
MS (FAB, glycerol): 667 (M+57).

EXAMPLE 35

[3-t-Butylsulfonyl,2-(2-thienylmethyl)]propionyl-Nva-[cyclohexylmethyl,(4,4,5,5-tetramethyl-1,3,2-dioxaborolane-2-yl)]methylamide The title compuond is prepared in analogy to example 1 from [3-t-Butylsulfonyl,2-(2-thienylmethyl)]propionyl-Nva-OH and the title compound of example 1a.

$R_f$(MTB) = 0.40  MS(FAB): 625(M + 1)

a) [3-t-Butylsulfonyl,2-(2-thienylmethyl)]propionyl-Nva-OH 490 mg of [3-t-Butylsulfonyl,2-(2-thienylmethyl)]-propionyl-Nva-OMe are dissolved in 4 ml of methanol, and 0.4 ml of H$_2$O and 0.7 ml of 2N NaOH are added and the mixture is stirred at R.T. for 5 h. The mixture is acidified to pH=2 with NaHSO$_4$ solution and extracted 3× with 50 ml of EA. The solution is then dried over Na$_2$SO$_4$, and the solvent is removed in vacuo. 470 mg of pale yellow resin are obtained.

$R_f$(EA) = 0.24   MS(FAB): 390(M + 1)

b) [3-t-Butylsulfonyl,2-(2-thienylmethyl)]propionyl-Nva-OMe 1,5 g of [3-t-Butylsulfonyl,2-(2-thienylmethyl)]propionic acid and 0.95 g of Nva-OMe×HCl dissolved in 40 ml of CH$_2$Cl$_2$ and, at 10° C., initially 3.8 ml of triethylamine, and then 3.5 ml of 50% solution of propane phosphonic anhydride in CH$_2$Cl$_2$ are added. The mixture is stirred at R.T. for 20 h, the solvent is removed in vacuo, the residue is taken up in 100 ml of MTB, and the solution is washed with 100 ml each of NaHSO$_4$ and NaHCO$_3$ solution. It is dried over Na$_2$SO$_4$, the solution is removed in vacuo, and the residue is chromatographed with EA/H 1:1. 2 diastereomeric oils are obtained and are further processed separately.

Diastereomer 1 $R_f$(EA/H 1:1) = 0.30   0.95 g

Diastereomer 2 $R_f$(EA/H 1:1) = 0.20   0.95 g

MS (DCI, the same for both diastereomers): 404 (M+1).

c) [3-t-butylsulfonyl,2-(2-thienylmethyl)]propionic acid 4.4 g of methyl [3-t-Butylsulfonyl,2-(2-thienylmethyl)]propionic acid are suspended in 50 ml of 5N HCL and refluxed for 2 h. After cooling, the mixture is extracted 3× with 50 ml of EA, the solution is dried over Na$_2$SO$_4$ and the solvent is removed in vacuo. 4.0 g of the title compound are obtained as a pale yellow oil.

$R_f$(MTB) = 0.15-0.25   MS(DCI): 291(M + 1)

d) Methyl [3-t-butylsulfonyl,2-(2-thienylmethyl)]-propionic acid 8.4 g of methyl [3-t-butylthio,2-(2-thenylmethyl)]-propionic acid are dissolved in 100 ml of CH$_2$Cl$_2$, and 10.6 g of m-chloroperbenzoic acid are added in portions while cooling in ice. The mixture is stirred at R.T. for 1 h and then washed first with 100 ml of 10% Na$_2$SO$_3$ and then with 100 ml of NaHCO$_3$. The solution is dried over Na$_2$SO$_4$, and the solvent is removed in vacuo. 7.2 g of the title compound are obtained as a colorless oil.

$R_f$(MTB) = 0.56   MS(DCI): 305(M + 1)

e) Methyl [3-t-butylthio,2-(2-thienylmethyl)]propionic acid 6.1 ml of t-butylmercaptan are dissolved in 100 ml of MeOH (anhydrous) and, under argon, 130 mg of NaH are added. Then 7.6 of methyl 2-(2-thienylmethyl)-acrylate are added dropwise and the mixture is stirred at R.T. for 4 h. The solvent is removed in vacuo, the residue is taken up in 100 ml of MTB and the solution is washed with 100 ml of 5% NaHSO$_4$ solution. It is dried over Na$_2$SO$_4$, and the solvent is removed in vacuo. 10.4 g of the title compound are obtained as a pale yellow liquid which is used further without purification and characterization.

R$_f$(DIP/H 1:5)=0.31.

f) Methyl 2-(2-thienylmethyl)acrylate 11.8 g of monomethyl 2-thienylmethylmalonate, 5.8 ml of diethylamine and 5.0 ml of 36% aqueous formaldehyde solution are stirred under argon at R.T. for 1 h. The water is subsequently removed in vacuo, and the residue is chromatographed. 7.6 g of the title compound are obtained as a colorless liquid.

R$_f$(MTB/H 1:5)=0.49.

g) Monomethyl 2-thienylmethylmalonate 20.1 g of dimethyl 2-thienylmethylmalonate are dissolved in 300 ml of MeOH, and 5.0 g of KOH are added. The mixture is stirred at R.T. for 7 h, the water is removed in vacuo, and the residue is taken up in 100 ml each of 5% Na$_2$CO$_3$ solution and EA. The aqueous phase is subsequently acidified to pH=2 and extracted 3× with 100 ml of EA each time. The solution is dried over Na$_2$SO$_4$, and the solvent is removed in vacuo. 16.0 g of the title compound are obtained as a pale yellow oil.

R$_f$(EA/MeOH 6:1)=0.3–0.4.

h) Dimethyl 2-thienylmethylmalonate 87.8 g of dimethyl malonate and 41.0 g of potassium t-butylate are dissolved in 1.1 l of THF (anhydrous) while cooling in ice, and, under argon, 44.1 g of 2-thienylmethylchloride in 500 ml of THF are added dropwise. The mixture is stirred at R.T. for 3 h, the KCL is removed by filtration, the solvent is removed in vacuo, and the residue is chromatographed. 33.8 g of the title compound (I) are obtained as a colorless oil, in addition to 8.8 g of dimethyl bis-(2-thienylmethyl)malonate (II)

R$_f$(I) (Toluene/DIP 20:1)=0.35.
R$_f$(II) (Toluene/DIP 20:1)=0.44.

g) (sic) 2-Thienylmethyl chloride 252 g of thiophene are suspended in 128 ml of concentrated aqueous HCl and, at 0° C., HCl gas is passed in for 1 h. Then, without interrupting the stream of HCl, 225 ml of 35% aqueous formaldehyde solution are added dropwise, and the mixture is stirred at 0° C. for a further 15 minutes. The organic phase is separated off and then the aqueous phase is extracted 2× with 600 ml of CH$_2$Cl$_2$. The solution is then washed 2× with 600 ml of saturated aqueous Na$_2$CO$_3$ and dried over Na$_2$SO$_4$, the solvent is removed in vacuo and the residue is distilled. 174 g of the title compound are obtained as a colorless liquid.

B.P.$_{22}$=81°–84° C.

The compounds of examples 36–44 (sic) are prepared in analogy to example 35.

EXAMPLE 36

(2-Benzyl,3-t-butylsulfonyl)propionyl-Nva-[cyclohexylmethyl,(4,4,5,5-tetramethyl-1,3,2-dioxaborolane-2-yl)]methylamide R$_f$(MTB) = 0.38    MS(FAB): 619(M + 1)

EXAMPLE 37

(3-t-Butylsulfonyl)propionyl-Nva-[cycloundecylmethyl, (4,4,5,5-tetramethyl-1,3,2-dioxaborolane-2-yl)]methylamide R$_f$(EA) = 0.24    MS(FAB): 559(M + 1)

EXAMPLE 38

(3-t-Butylsulfonyl)propionyl-Nva-[1-napthylmethyl, (4,4,5,5-tetramethyl-1,3,2-dioxaborolane-2-yl)]methylamide R$_f$(EA) = 0.23    MS(FAB): 573(M + 1)

EXAMPLE 39

(2-Benzyl,3-t-butylsulfonyl)propionyl-Val-[cyclohexylmethyl,(4,4,5,5-tetramethyl-1,3,2-dioxaborolane-2yl)]methylamide R$_f$(MTB) = 0.25    MS(FAB): 619(M + 1)

EXAMPLE 40

[3-t-Butylsulfonyl,2-(2-thienylmethyl)]propionyl-thi[cycloheptylmethyl,(4,4,5,5-tetramethyl-1,3,2-dioxaborolane-2-yl)]methylamide R$_f$(EA/H 1:1) = 0.23    MS(FAB): 693(M + 1)

EXAMPLE 41

[3-t-Butylsulfonyl,2-(2-thienylmethyl)]propionyl-Nva-[cycloheptylmethyl,(4,4,5,5-tetramethyl-1,3,2-dioxaborolane-2-yl)]methylamide R$_f$(MTB) = 0.35    MS(FAB): 639(M + 1)

EXAMPLE 42

[3-t-Butylsulfonyl,2-(1-naphthylmethyl)]propionyl-Nva-[3-methyl,1-(4,4,5,5-tetramethyl-1,3,2-dioxaborolane-2-yl)]butylamide R$_f$(MTB) = 0.26    MS(FAB): 629(M + 1)

EXAMPLE 43

[3-t-Butylsulfonyl,2-(2-thienylmethyl)]propionyl-Thi-[cyclohexylmethyl,(4,4,5,5-tetramethyl-1,3,2-dioxaborolane-2-yl)]methylamide R$_f$(MTB) = 0.53    MS(FAB) 679(M + 1)

EXAMPLE 44

(2-Benzyl,3-t-butylsulfonyl)propionyl-Nva-[cyclopentylmethyl,(4,4,5,5-tetramethyl-1,3,2-dioxaborolane-2-yl)]-methylamide R$_f$(MTB) = 0.36  MS(FAB): 605(M + 1)

EXAMPLE 45

[3-Butylsulfonyl,2-(2-methyl)benzyl]propionyl-Nva-[cyclohexylmethylo,(4,4,5,5-tetramethyl-1,3,2-dioxaborolane-2-yl)]methylamide R$_f$(MTB) = 0.40  MS(FAB): 633(M + 1)

EXAMPLE 46

[3-t-Butylsulfonyl,2-(3-methyl)benzyl]propionyl-Nva-[cyclohexylmethyl,(4,4,5,5-tetramethyl-1,3,2-dioxaborolane-2-yl)]methylamide R$_f$(MTB) = 0.40  MS(FAB): 633(M + 1)

EXAMPLE 47

(2-Benzyl,3-t-butylsulfonyl)propionyl-Nva-[benzyl,(4,4,5,5-tetramethyl-1,3,2-dioxaborolane-2-yl)[methylamide R$_f$(MTB) = 0.30  MS(FAB): 613(M + 1)

EXAMPLE 48

(2-Benzyl,3-t-butylsulfonyl)propionyl-Asn-[benzyl,(4,4,5,5-tetramethyl-1,3,2-dioxaborolane-2-yl)[methylamide R$_f$(EA) = 0.05  MS(FAB): 628(M + 1)

EXAMPLE 49

(2-Benzyl,3-t-butylsulfonyl)propionyl-Nva-[cycloheptyl,(4,4,5,5-tetramethyl-1,3,2-dioxaborolane-2-yl)[methylamide R$_f$(MTB) = 0.30  MS(FAB): 619(M + 1)

EXAMPLE 50

[3t-Butylsulfonyl,2-(1-naphthylmethyl)]propionyl-Nva-(cyclopentylmethyl,(4,4,5,5-tetramethyl-1,3,2-dioxaborolane-2-yl]-methylamide R$_f$(MTB) = 0.40  MS(FAB): 655(M + 1)

EXAMPLE 51

[3-t-Butylsulfonyl,2-(1-naphthylmethyl)]propionyl-Nva-[3-ethyl,1-(4,4,5,5-tetramethyl-1,3,2-dioxaborolane-2-yl)]-pentylamide R$_f$(MTB) = 0.50  MS(FAB): 657(M + 1)

EXAMPLE 52

(2-Benzyl,3-t-butylsulfonyl)propionyl-Nvu-[3-ethyl,1-(4,4,5,5-tetramethyl-1,3,2-dioxaborolane-2-yl)]pentylamide R$_f$(MTB) = 0.44  MS(FAB): 607(M + 1)

EXAMPLE 53

(2-Benzyl,3-t-butylsulfonyl)propionyl-Nva-[3-methyl,1-(4,4,5,5-tetramethyl-1,3,2-dioxaborolane-2-yl)]butylamide R$_f$(MTB) = 0.35  MS(FAB): 579(M + 1)

EXAMPLE 54

(3-t-Butylsulfonyl,2-(2-thienylmethyl)]propionyl-Asn-[cyclohexylmethyl,(4,4,5,5-tetramethyl-1,3,2-dioxaborolane-2-yl)]methylamide R$_f$(EA/acetone 5:1)=0.30′ MS (FAB): 640 (M+1)

We claim:

1. A compound of the formula I

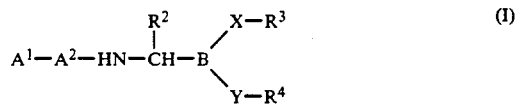

in which

A$^1$ is a radical of the formulae II or III,

in which

R$_1$ is (C$_1$-C$_8$)-alkylsulfonyl; (C$_1$-C$_8$)-alkylsulfinyl; (C$_1$-C$_{11}$)-alkanoyl; (C$_3$-C$_9$)-cycloalkylcarbonyl; (C$_6$-C$_{10}$)-aryl-(C$_2$-C$_{11}$)-alkanoyl; 2-pyridyl-(C$_1$-C$_8$)-alkanoyl; 3pyridyl-(C$_1$-C$_8$)-alkanoyl; 4-pyridyl-(C$_1$-C$_8$)-alkanoyl; pyrrolyl-2-carbonyl; pyridyl-3-carbonyl; benzenesulfonyl; (C$_1$-C$_{10}$)-alkoxycarbonyl; 2-(trimethylsilyl)-ethoxycarbonyl; 2,2,2-trichloroethoxycarbonyl; 1,1-dimethyl-2,2,2-trichloroethoxycarbonyl; (C$_6$-C$_{14}$)-aryl-(C$_1$-C$_6$)-alkoxycarbonyl, R$^2$ is mono- or bicyclic (C$_3$-C$_{18}$)-cycloalkyl or (C$_3$-C$_{18}$)-cycloalkylmethyl, the cycloalkyl moiety optionally being substituted by (C$_1$-C$_4$)-alkyl;

R$^3$ and R$^4$ are hydrogen, or form, together with boron, X and Y, a mono-, bi- or tricyclic mono-, di-, tri- or tetra-(C$_1$-C$_{12}$)-alkylated, saturated or partially unsaturated ring system which as 5–18 ring members and, apart from boron, X, Y and carbon, can also contain an —O— member, an —NR$^{13}$- member, or a —CR$^{14}$R$^{15}$-member, X and Y are —O—, R$^5$ is isopropyl, n-propyl, n-butyl, isobutyl, sec.-butyl, carbamoylmethyl, 2-carbamoylethyl, mercaptomethyl, 2-(methylthio)ethyl, (1-mercapto,1- methyl)-ethyl, hydroxymethyl, 1-hydroxyethyl, cyclohexylmethyl, 4-imidazolylmethyl, benzyl, 2-methylbenzyl, 3-methylbenzyl, 3-indolylmethyl, 4-hydroxybenzyl, 4-methoxybenzyl, 3,4-dihydroxybenzyl, 3,4-dimethoxybenzyl, (benzodioxolane-5-yl)methyl, 2-thienyl, 2-thienylmethyl, 2(2-thienyl)-ethyl, 3-thienyl, 3-thienylmethyl, 2(3-thienyl)ethyl, 4-chlorobenzyl, 2-(methylsulfinyl)ethyl, 2-(methylsulfonyl)ethyl, 2-pyridylmethyl, 3-pyridylmethyl, 4-pyridylmethyl, cyclohexyl, (1-methyl-4-imidazoyl)methyl, (3-methyl-4-imidazolyl)methyl, phenyl, 1-naphthylmethyl, 2-naphthylmethyl, 2-phenylmethyl, 2-thiazolylmethyl, 4-thiazolylmethyl, 3-pyrazolylmethyl, 4-pyrimidinylmethyl, 2-indolylmethyl, 2-benzo[b]thienylmethyl, or 3-benzo[b]thienylmethyl, $R^6$ is hydrogen, $R^{12}$ is hydrogen or methyl or forms, together with $R^1$, a mono- or bicyclic saturated or partially unsaturated ring system which has 5-12 ring members and, apart from carbon, can also contain 1 sulfur atom which can optionally be oxidized to the sulfoxide or sulfone, $R^{13}$ is hydrogen or $(C_1-C_4)$-alkyl, $R^{14}$ and $R^{15}$ are, independently of one another, hydrogen, $(C_1-C_8)$-alkyl, hydroxymethyl, 2-hydroxyethyl, (3-hydroxysulfonyl, 2-hydroxypropyl)amino, (2-hydroxysulfonylethyl)amino, (2-hydroxysulfonylpropyl)amino, (carboxymethyl)amino, or bis(2-hydroxyethyl)amino, $A^2$ is a radical which is linked N-terminal to $A^1$ and C-terminal to the amino boronic acid derivative and has the formula VIII,

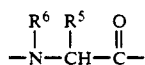

(VIII)

$R^5$ and $R^6$ being defined as above, as well as the physiologically tolerated salts thereof.

2. A compound of the formula I as claimed in claim 1 in which:

$A^1$ represents a radical of the formula II or III in which $R^1$ denotes $(C_1-C_6)$-alkylsulfonyl; $(C_1-C_6)$-alkylsulfinyl; $(C_1-C_6)$-alkoxycarbonyl; $(C_6-C_{10})$-aryl-$(C_1 \propto C_6)$-alkoxycarbonyl, $R^2$ denotes $(C_5-C_8)$-cycloalkyl; $(C_5-C_{11}$-cycloalkylmethyl; $[(C_1-C_4)$-alkyl-cyclohexyl]methyl;

$R^3$ and $R^4$ represent hydrogen, or form, together with boron, X and Y, a 1,3,2-dioxaborolane radical which is optionally substituted by 1 to 4 methyl groups, a [4,5-diisopropyl]-1,3,2-dioxaborolane, a [(N-B)-(2,2'-imino-diethanolato)-boryl)], a pinandioxyboryl or a 1,3,2-dioxaborinane radical whose carbon atom in position 5 is substituted by $R^{14}$ and $R^{15}$, X and Y represent —O—, $R^5$ denotes n-propyl, isopropyl, n-butyl, isobutyl, sec.-butyl, carbamoylmethyl, 2-carbamoylethyl, benzyl, 2-methylbenzyl, 3-methylbenzyl, 2-thienylmethyl, 3-thienylmethyl, 1-naphthylmethyl, 2-naphthylmethyl, imidazol-4-yl-methyl or 2-thiazolylmethyl, $R^6$ represents hydrogen, $R^{12}$ denotes hydrogen, $R^{14}$ and $R^{15}$ denote, independently of one another, hydrogen, $(C_1-C_8)$-alkyl, hydroxymethyl, 2-hydroxyethyl, (3-hydroxysulfonyl, 2-hydroxypropyl)-amino, (2-hydroxysulfonylethyl)amino, (2-hydroxysulfonylpropyl)amino, (carboxymethyl)amino or bis(2-hydroxyethyl)amino, and $A^2$ represents a radical of the formula VIII, with $R^5$ and $R^6$ being defined as above, and the physiologically tolerated salts thereof.

3. A method for the treatment of high blood pressure, which comprises administration of an effective amount of a compound of the formula I as claimed in claim 1, or a physiologically tolerated salt thereof.

4. A pharmaceutical composition for the treatment of high blood pressure comprising an effective amount of a compound of the formula I as claimed in claim 1, or a physiologically tolerated salt thereof, and a pharmaceutically acceptable vehicle.

* * * * *